United States Patent [19]

Gruber et al.

[11] Patent Number: 5,236,908
[45] Date of Patent: Aug. 17, 1993

[54] METHODS OF TREATING INJURY TO THE CENTRAL NERVOUS SYSTEM

[75] Inventors: Harry E. Gruber, San Diego; Leonard P. Miller, Carlsbad, both of Calif.

[73] Assignee: Gensia Pharmaceuticals, Inc., San Diego, Calif.

[21] Appl. No.: 712,158

[22] Filed: Jun. 7, 1991

[51] Int. Cl.$^5$ ............................................ A61K 31/70
[52] U.S. Cl. ...................................................... 514/46
[58] Field of Search ........................................ 514/46

[56] References Cited

PUBLICATIONS

Chem. Abst(1)-109-183464R (1988).
Chem. Abst(2)-111-187408Q (1989).
Chem. Abst(3)-113-184571t (1990).

Primary Examiner—S. J. Friedman
Attorney, Agent, or Firm—Lyon & Lyon

[57] ABSTRACT

The invention provides methods for preventing neural tissue damage caused by injury to the central nervous system (CNS) by the administration of a therapeutically effective amount of an adenosinergic agent. One aspect of the invention is directed toward continuous administration of a therapeutically effective amount of an adenosinergic agent for a period of time sufficient to prevent neural tissue damage. In another aspect of the present invention, the adenosinergic agents may be administered on several occasions during the prolonged period of treatment, so long as the doses of adenosinergic agents are spaced in time so that a therapeutically effective concentration of adenosinergic agent is maintained for a period of time sufficient to prevent neural tissue damage.

31 Claims, 13 Drawing Sheets

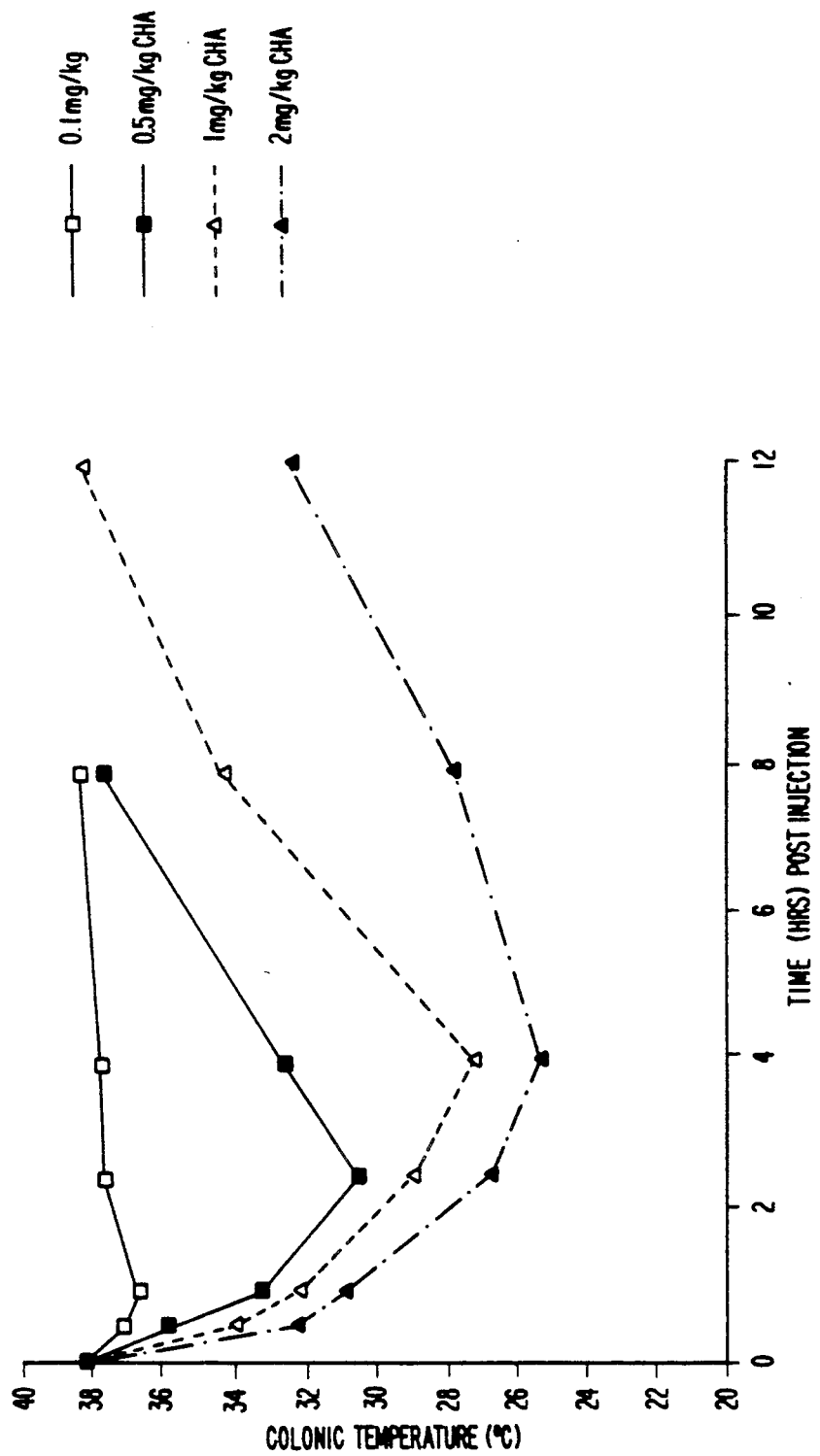

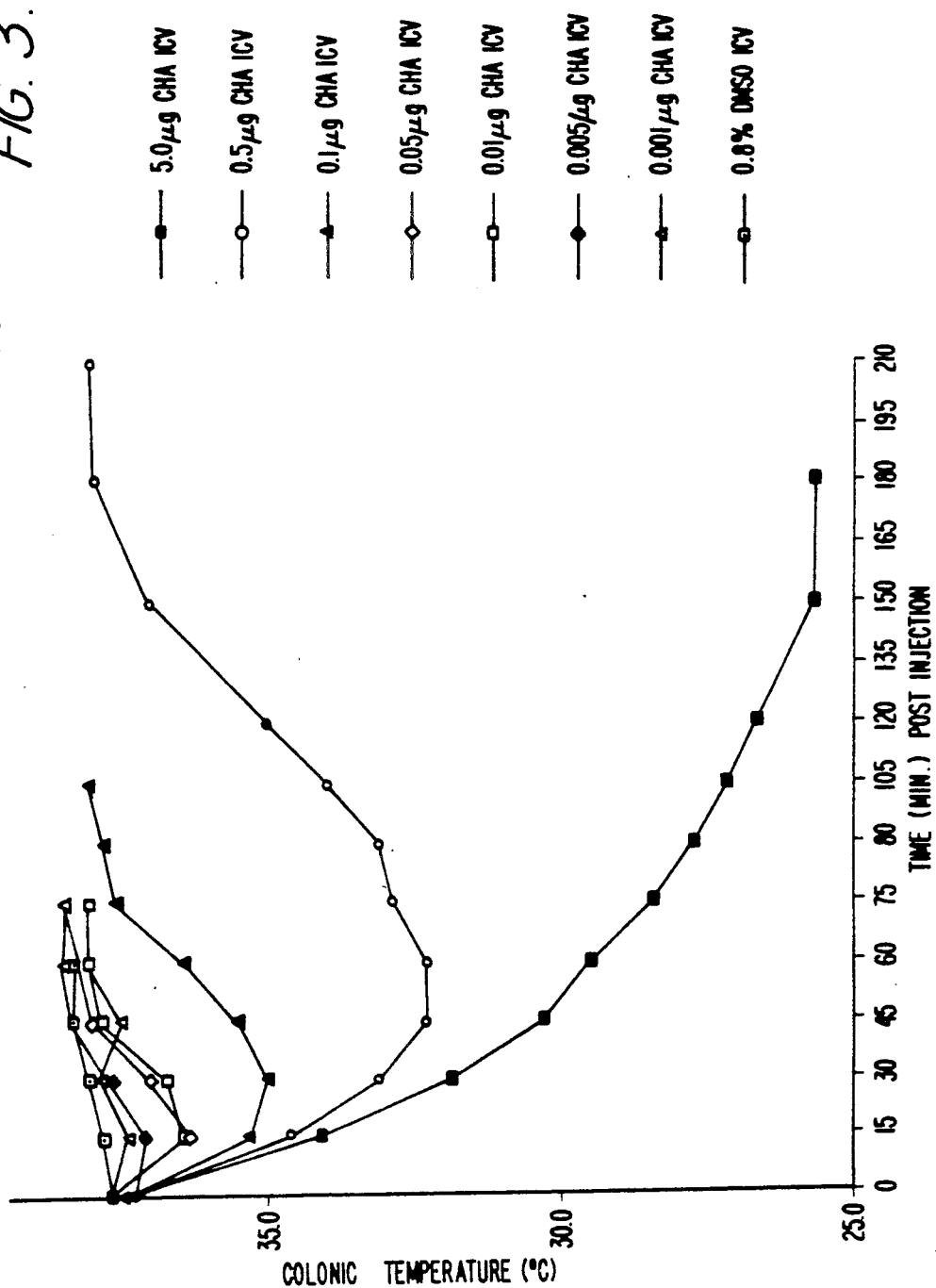

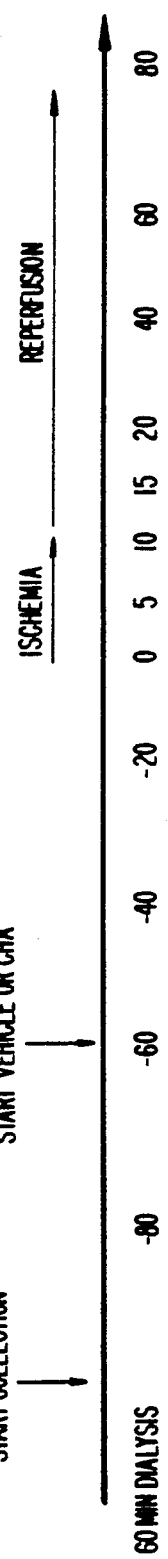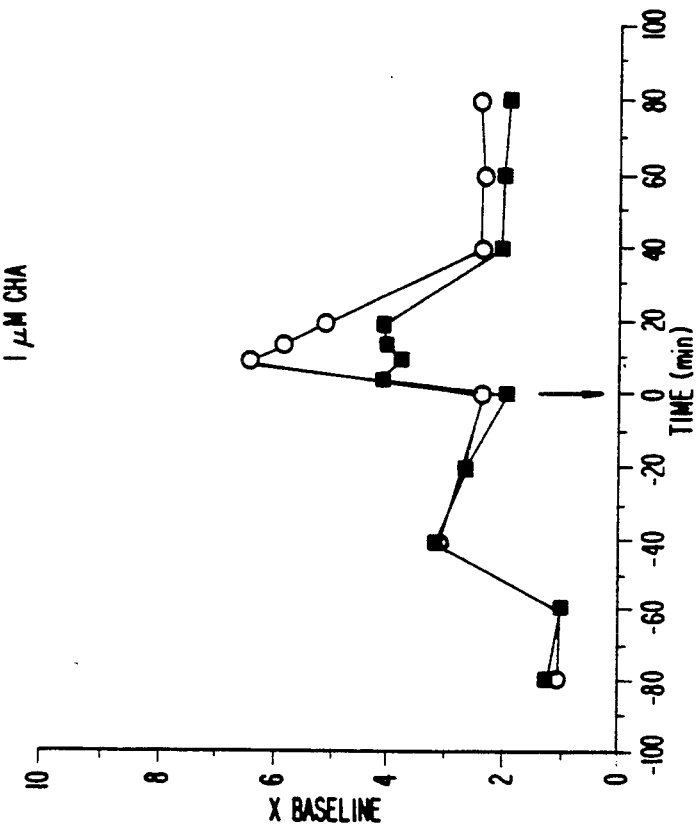
FIG. 5.
FIG. 6.

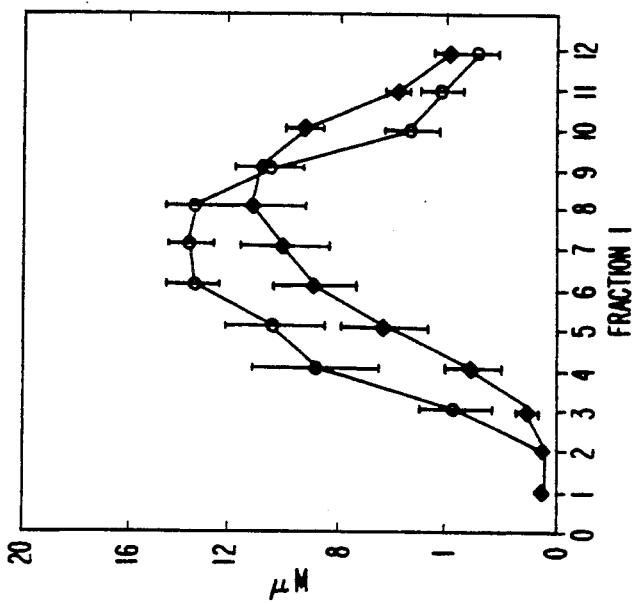
FIG. 8d. CONTROL VS. CHA(-6M)
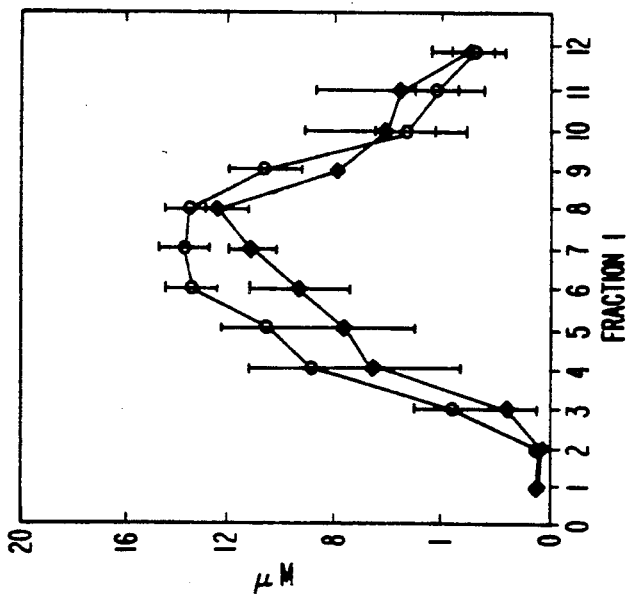
FIG. 8c. CONTROL VS. CHA(-7M)

HIPPOCAMPAL GLYCINE CONCENTRATIONS

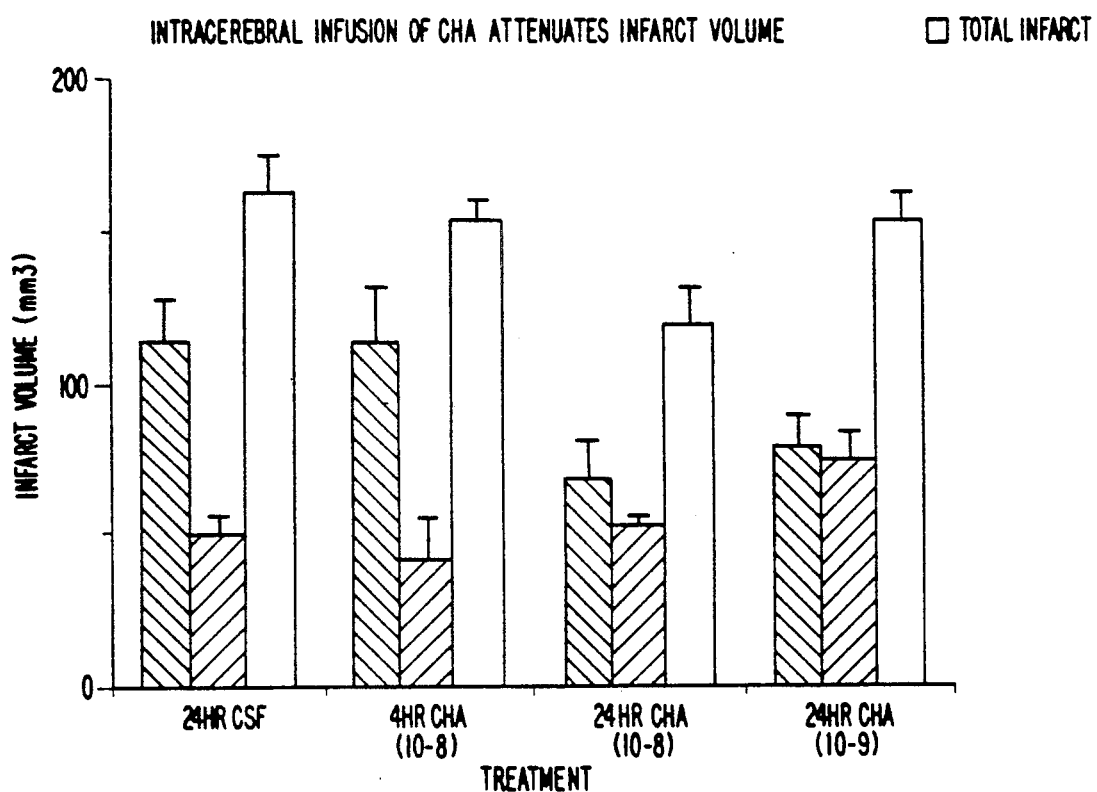
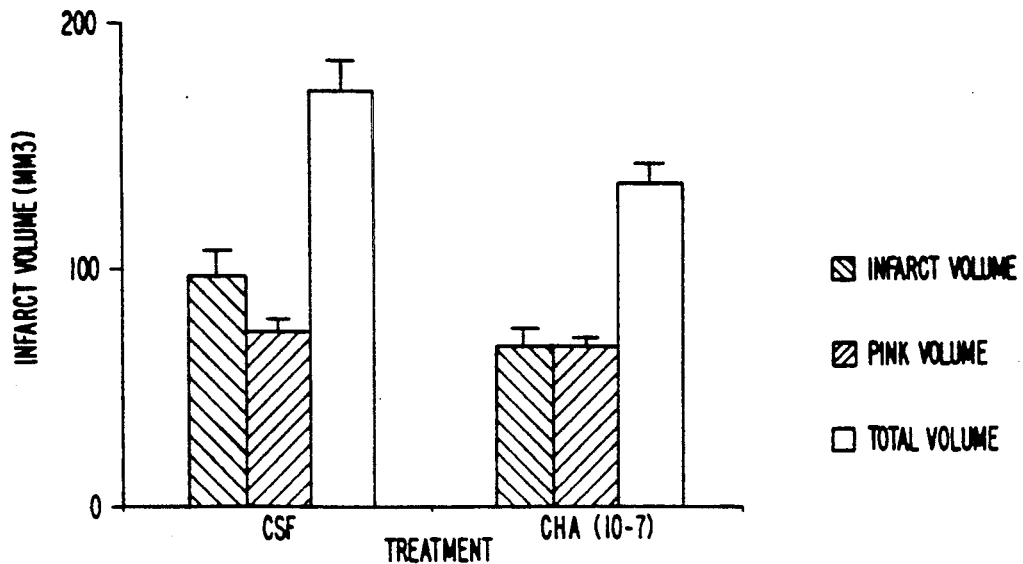

METHODS OF TREATING INJURY TO THE CENTRAL NERVOUS SYSTEM

FIELD OF THE INVENTION

The present invention is in the field of medicine, more particularly, the field of clinical neurology, and relates specifically to methods of treating injury to the central nervous system (CNS). As used herein, injury is meant to include, but is not limited to, global focal ischemia, stroke (including ischemic or hemorrhagic), generalized brain or spinal cord trauma or chronic injury in diseases such as Alzheimer's Disease, Amyotrophic Lateral Sclerosis, Huntington's Chorea or Parkinson's Disease in warm-blooded animals.

BACKGROUND OF THE INVENTION

Present therapy for clinical management of brain injury, such as stroke, is directed toward maintaining blood flow to the brain and preventing further damage. In the case of an infarct or stroke, anticoagulants such as heparin and warfarin may be prescribed for short-term use to prevent blood clots from becoming larger. Aspirin or warfarin may also be used by certain stroke patients to prevent future strokes. Other therapy involves the application of thrombolytics for dissolving clots. With hemorrhagic stroke, drugs are administered to control brain swelling, high blood pressure and vasospasm.

It has been reported that extracellular levels of the excitatory amino acids (EAAs), glutamate and aspartate, increase 4-10 fold (Benveniste, H. et al., *J. Neurochem.* 1984 43:1369-1374) during or shortly following neuroinjury, resulting in indiscriminate and continuous activation of postsynaptic EAA receptors. This elevation of extracellular EAA levels is thought to be part of the periphenomena of most acute neuroinjury events, and may be one of the initial mechanisms in the cascade of events leading to cell damage. (Rothman and Olney, *Trends Neurosci.* 1987 10:299-302). This continuous EAA-mediated neurotransmission which results in cell death has been termed excitotoxicity (Olney, *J. Neuropathol. Exp. Neurol.* 1971 30:75-90). It has been reported that excessive activation of EAA receptors results in sustained elevated intracellular levels of $Ca^{++}$ at the post-synaptic site, and that this increase in intracellular $Ca^{++}$ activates numerous intracellular enzymes, including proteases, lipases and kinases (see FIG. 1) (Choi, *Neurosci. Lett.*, 1985, 58:293-297). If unabated, combined and persistent activation of these intracellular mechanisms leads to loss of cellular integrity and eventual cell death.

EAA receptors have been grouped into four subtypes: (1) n-methyl-d-aspartate (NMDA); (2) kainic acid (KA); (3) alpha-amino-3-hydroxy-5-methyl-4-isoxazole propionic acid (AMPA); and (4) trans-amino-1,3-cyclopentanedicarboxylic acid (ACPD) (Marangos and Miller, 1991, in *Adenosine and Adenine Nucleotides as Regulators of Cellular Function*, ed. J. Phillis, p.360-365). Glycine has been reported to modulate NMDA receptor-mediated neurotransmission (Johnson, J. W. and Ascher, P., *Nature* 1987 325:529-531). It has also been reported that glycine is an obligatory component for NMDA receptor function (Kleckner and Dingledine, *Science* 1988 241:835-837).

Two different animal models of stroke are currently used in preclinical studies: global ischemia and focal stroke. Global ischemia results in complete loss of blood flow to the brain and complete loss of energy reserves and ion homeostasis. This model is generally more analogous to strokes occurring as a result of revival from a heart attack, cardiopulmonary arrest, strangulation or short-term interruption of blood flow to the brain.

In the global brain ischemia model the time period over which cell loss occurs has been reported to vary (Smith et al., *Acta Neuropathologica*, 1984 64:319-332; Kirino et al., *Brain Res.*, 1982 239:57-69). In addition, it has been reported that there are regions of the brain which are selectively sensitive to ischemia-induced mechanisms. For example, it has been reported that cell death appears within hours in the hippocampal CA4 subregion, within a day in the striatum (Crain et al., *Neuroscience*, 1988 27:387-402), and over a period of 2-3 days within the hippocampal CA1 region.

Focal stroke is a better model than global ischemia for a majority of human strokes of thromboembolic origin or associated with the surgical procedures such as carotid endarterectomy or coronary artery bypass graft (CABG). A focal stroke is characterized by a gradient of blood flow from near total cessation in the central area of a blood vessel's territory of distribution to normal or increased flow at the periphery. Cell damage is confined to a region of the cortex within which a small core area is unsalvageable but a peripheral region (called the penumbra) is redeemable. Neuronal activity throughout the region is depressed, while ion homeostasis is maintained or intermittently disrupted in the penumbra region by periods of depressed neuronal activity, also known as waves of spreading depression.

It has been reported that adenosine inhibits EAA release (Burke and Nadler, *J. Neurochem.* 1988 51:1541-1551) (See FIG. 1). Adenosine acts at the level of the cell plasma membrane by binding to receptors. In both the brain and peripheral tissue these receptors have been designated as purinergic ($P_1$) receptors (Burnstock, *Pharmacol. Rev.*, 1972 24:509), which have been further classified into $A_1$ and $A_2$ receptor subtypes (Daly et al., *Cell. Mol. Neurobiol.* 1983 3:69-80). $A_1$ and $A_2$ receptor subtypes have been defined on the basis of their effect on cyclic adenosine 5'-monophosphate (cAMP) production and their structure activity relationships (Trevedi, et al., "Structure-Activity Relationships of Adenosine $A_1$ and $A_2$ Receptors," *Adenosine and Adenosine Receptors*, (Williams, M. 1990)). For example, $A_1$ agonists are characterized by their ability to displace N-6 cyclohexyladenosine (CHA) specifically bound to the $A_1$ receptor in membranes prepared from the cortex of rat brains. $A_2$ agonists are characterized by their ability to displace N-ethylcarboxamido adenosine (NECA). Applicants have demonstrated that inhibition of EAA release in vivo results from $A_1$ receptor activation. Adenosine agonists have affinity for both $A_1$ and $A_2$ receptors with some showing a greater affinity for $A_1$ than $A_2$ receptors. However, known $A_1$-specific agonists will react with $A_2$ receptors when the $A_1$ agonist concentration is sufficiently elevated so as to achieve a local concentration which is effective at the $A_2$ receptor.

Several investigators have observed efficacy in the global ischemia and focal stroke models upon application of adenosine regulating compounds, adenosine agonists and transport inhibitors. The following investigations were carried out using a global ischemia model. Studies have examined compounds which increase adenosine levels by inhibition of adenosine deaminase (Phillis, J. W. and O'Regan M. H., *Brain Res. Bull.* 1989 22:537–540), purine nucleoside phosphorylase (Phillis, J. W. et al., *Int. J. Purine & Pyrimidine Res.* 1990 1:19–23) and xanthine oxidase (Phillis, J. W., *Brain Res. Bull.* 1989 23:467–470 and Helfman, C. and Phillis, J. W., *Med. Sci. Res.* 1989 17:969–970). Investigations with adenosine agonists have included cyclohexyl adenosine (CHA) (Von Lubitz DKJE et al., *Stroke* 1988 19:1133–1139: Daval, J. L. et al., *Brain Res.* 1989 491:212–226) 2-chloroadenosine (Evans, M. C. et al., *Neurosci Letts.* 1987 83:287–292) and L-phenylisopropyladenosine (Block G. A. and Pulsinelli, *J. Cere. Blood Flow Metabol.* 1987, 7(suppl 1):S258). The transport inhibitor propentofylline has also been reported to be efficacious in the global ischemia model (DeLeo J. et al., *Neurosci Letts.* 1988 84:307–311; DeLeo, J. et al., *J. Cereb. Blood Flow Metab.* 1987 7:745–751; DeLeo, J. et al., *Stroke* 19:1535–1539: Hagberg, H. et al. in *Pharmacology of Cerebral Ischemia*, eds J. Krieglstein & H. Oberpichler, 1990, 427–437; Dux e. et al., *Brain Res.* 1990, 516:248–256). Another study examined adenosine agonist, R-phenylisopropyladenosine, in a focal stroke model and reported neuroprotection (Bielenberg G. W., *J. Cere. Blood Flow Metabol.* 1989, 9(supp 1):S645).

In one study, using a global stroke model, injections of 2-chloroadensine (2CLA) directly into the hippocampus were examined (Evans M. C., Swan, J. H. and Meldrum, B. S., *Neurosci Letts.* 1987 83:287–292). In these experiments efficacy was examined with iterative injections of 2CLA (a) immediately before a 10 minute period of ischemia and then at 4 and 10 hours into reperfusion, (b) at 1 minute, 4 and 10 hours into reperfusion, and (c) at 10 and 24 hours into reperfusion. It was reported that 2CLA protected against cell loss in protocols (a) and (b), but not in protocol (c).

SUMMARY OF THE INVENTION

The present invention is directed to methods of preventing neural tissue damage associated with injury to the central nervous system including, among others, stroke, brain trauma, and injury occurring during surgery (such as during carotid endarterectomy). Applicants have discovered that prolonged treatment with adenosinergic agents provides protection from damage to neural tissue resulting from injury to the CNS. By prolonged treatment is meant a time period sufficient to prevent neural tissue damage, for example, in experiments using CHA described herein, a treatment period of more than 4 hours is required to prevent neural tissue damage. Of course, the time period sufficient to prevent neural tissue damage may vary depending on several factors, including the particular compound and dosage used. Preferably the time period sufficient to prevent neural tissue damage is a time period of longer than four hours, more preferably for a period of longer than 8 hours, more preferably for a period of 12 hours, more preferably for a period of longer than 24 hours, and more preferably for a period of longer than 48 hours.

The maintenance of effective concentrations of adenosinergic agents can be accomplished by continuous administration or by repeated doses of the agents. The particular method chosen may depend, among other factors, on the biological half-life of the adenosinergic agent used. For example, continuous administration would be needed to maintain an effective concentration of a compound having a short biological half-life, while repeated doses may be sufficient for a compound having a longer biological half-life.

By protection from damage to neural tissue is meant reduction in the total stroke volume and/or infarct volume following injury to the CNS, preferably as manifested by less neurological and/or cognitive deficits.

Thus, the invention provides methods for preventing neural tissue damage caused by injury to the central nervous system (CNS) by the administration of a therapeutically effective amount of an adenosinergic agent. One aspect of the invention is directed toward continuous administration of a therapeutically effective amount of an adenosinergic agent for a period of time sufficient to prevent neural tissue damage.

In another aspect of the present invention, the adenosinergic agents may be administered on several occasions during the prolonged period of treatment, so long as the doses of adenosinergic agents are spaced in time so that a therapeutically effective concentration of adenosinergic agent is maintained for a period of time sufficient to prevent neural tissue damage. Preferably, the adenosinergic agents are administered so that a concentration of equivalent potency to CHA at $10^{-9}$M to $10^{-6}$M is maintained throughout the treatment period. More preferably, the adenosinergic agents are administered so that a concentration of equivalent potency to a concentration of CHA at from $10^{-8}$M to $10^{-7}$M is maintained throughout the treatment period. By equivalent potency is meant equivalent effective potency at the site of neural injury. The effective potency of compounds is a function of binding affinity to $A_1$ receptors as well as ability to attenuate EAA release. Those skilled in the art would be aware of methods of performing binding studies. (See. e.g., Daly, et al., *Cell Mol Neurobiol.* 1983 3:69–80). Examples 2 and 3 herein describe methods of measuring ability of compounds to attenuate EAA release.

In all aspects, the administration of an adenosinergic agent may be initiated prior to injury or after injury, depending on the circumstances. For example, administration of an adenosinergic agent may be begun prior to surgery likely to cause an ischemia and then continued during surgery and for a period of time thereafter sufficient to prevent injury to the CNS.

A preferred group of adenosinergic agents are adenosine regulating agents (ARAs), which include 5-aminoimidazole-4-carboxamide (AICA) riboside and its prodrugs and analogs, which cause site-specific and event-specific adenosine elevations, thus avoiding the unwanted global action of other adenosinergic agents.

Because many cells in the body have functional receptors for adenosine, techniques that increase adenosine concentrations generally throughout the body can cause unwanted, dramatic changes in normal cellular physiology. (See *Purine Metabolism in Man*, (eds. De Baryn, Simmonds and Muller), Plenum Press, New York (1984)). In addition, adenosine deaminase inhibitors prevent the degradation of deoxyadenosine, which is a potent immunotoxin. (see Gruber et al., *Ann. New York Acad. Sci.* 451:315–318 (1985)).

Accordingly, adenosinergic agents which selectively increase extracellular adenosine levels in the areas of the CNS affected by trauma, such as ischemia, are preferred. Thus, a preferred aspect of the methods of the present invention is directed to the use of adenosine regulating agents which selectively enhance extracellular adenosine concentration in neural tissue to protect against or lessen damage to neural tissue.

Other preferred ARAs include enzyme inhibitors which lead to elevated levels of extracellular adenosine in the CNS, such as adenosine kinase inhibitors and AMP deaminase inhibitors.

Another group of preferred adenosinergic agents is adenosine transport inhibitors, including competitive inhibitors of adenosine transport as well as compounds which inhibit adenosine transport nonspecifically.

Another preferred group of adenosinergic agents are adenosine agonists. Particularly preferred are $A_1$ adenosine agonists, especially those which readily cross the blood brain barrier. Also preferred are adenosine agonists which have lower dromotropic (conduction) effects on the heart compared to agonist activity in the brain. Particularly preferred are those adenosine agonists which are more potent at the $A_1$ site, as demonstrated by having a binding affinity at the $A_1$ receptor of greater than about 400 times their binding affinity at the $A_2$ receptor. Most preferred are those adenosine agonists which have a binding affinity at the $A_1$ receptor of greater than about 800 times their binding activity at the $A_2$ receptor.

Another group of preferred adenosinergic agents are compounds which enhance the binding or intrinsic activity of either adenosine or adenosine agonists at $A_1$ receptors.

The adenosinergic agents of the present invention may be effectively administered in amounts ranging from 0.001 mg/kg/day to about 500 mg/kg/day; preferably from about 1 mg/kg/day to about 200 mg/kg/day. For Al agonists, a dosage of from 0.01 mg/kg/day to 10 mg/kg/day is preferred.

One aspect of the present invention is directed to the use of adenosinergic agents which when administered IV will cross the blood brain barrier to a sufficient extent to allow interaction at adenosinergic receptors within the CNS. Preferably, the adenosinergic agents will have CSF concentrations of 10% or greater compared to plasma concentrations.

In a preferred embodiment of the present invention, adenosinergic agents are administered with adenosine-receptor antagonists.

Other aspects of the present invention include a composition adapted for prolonged release of an adenosinergic agent and an apparatus for prolonged administration of an adenosinergic agent.

BRIEF DESCRIPTION OF THE DRAWINGS

FIG. 2 depicts the time course effect of CHA administered intraperitoneally (IP) on colonic temperature.

FIG. 3 depicts the effect of CHA administered intracerebroventricularly (ICV) on colonic temperature.

FIG. 5 depicts the temporal sequence of events of the experiments described in EXAMPLES 2 and 3. Initiation of ischemia is designated t=0.

FIG. 6 depicts the brain extracellular glutamate concentrations collected using a microdialysis probe in the presence and absence of 1 μM CHA over the temporal sequence as described in FIG. 5. Amino acid levels recorded on the y-axis are normalized to the level of glutamate obtained at t= −60.

FIG. 11 depicts the effect of various periods (4 and 24 hours) of direct cortical infusion with CHA at $10^{-8}$M and the effect of various concentrations of CHA ($10^{-9}$ and $10^{-8}$M) infused over 24 hours on infarct volume in rat. Procedure is described in Example 5. Pink volume denotes region of presumed partial injury. * designates significance of $p<0.05$ versus control.

FIG. 12 depicts the effect of CHA at $10^{-7}$M infused over 24 hours on infarct volume in rat. Procedure is described in Example 5. * designates significance of $p<0.05$ versus control.

DETAILED DESCRIPTION OF THE INVENTION

Adenosinergic Agents

Figure 1:
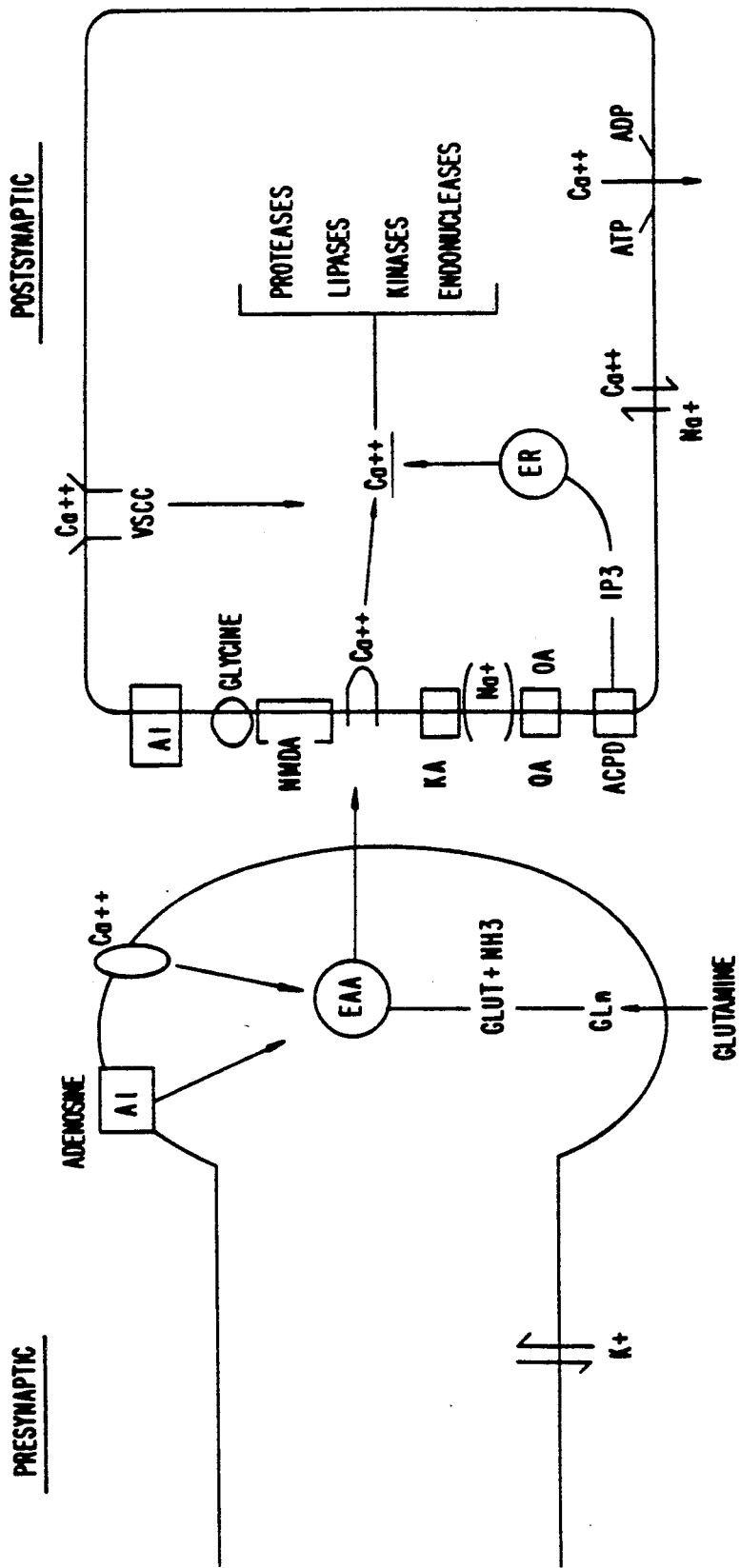
FIG. 1 schematically illustrates the sites of action of adenosine or adenosine agonists on neural tissue.

The term "adenosinergic agent" refers to one or a combination of the following: (1) adenosine agonists, (2) adenosine regulating agents (ARAs), such as enzyme inhibitors and enzyme activators, (3) adenosine transport inhibitors, and (4) enhancers which increase binding or intrinsic activity of agonists at the receptor.

(1) Adenosine agonists include adenosine analogs which have structural modifications in the purine ring, alterations in substituent groups attached to the purine ring, and modifications or alterations in the site of attachment of the carbohydrate moiety, leading to increased binding at the $A_1$ receptor. Adenosine agonists especially $A_1$ agonists are preferred compounds. Adenosine agonists which are about 400 fold more potent at the $A_1$ versus the $A_2$ site are particularly preferred to allow complete activation of the $A_1$ receptor with little or no activation of the $A_2$ receptor. This should allow maximal activation of the $A_1$ receptor without activation of the $A_2$ receptor and therefore maximally inhibits EAA release and also minimize untoward $A_2$ related side-effects. Preferably, these compounds will have good blood brain barrier penetration (CSF concentrations 10% or greater compared to plasma concentrations). Examples of active compounds include CHA, phenylisopropyladenosine, cyclopentyladenosine and 2 chloroadenosine.

(2) Adenosine regulating agents (ARAs) include inhibitors of adenosine catabolism and enhancers of adenosine production.

Examples of compounds useful as adenosine regulating agents in the methods of the present invention include compounds broadly classified as purine nucleosides and related analogs, such as AICA riboside, and its prodrugs and analogs. Certain purine prodrugs and analogs which exhibit and, in some cases improve on, the positive biological effects of AICA riboside and other adenosine regulating compounds without the negative effects of adenosine are disclosed in the commonly assigned pending patent applications "AICA Riboside Prodrugs," U.S. Ser. No. 301,222, filed Jan. 24, 1989; "Method and Compounds for AICA Riboside Delivery and for Lowering Blood Glucose," U.S. Ser. No. 408,107, filed Sep. 15, 1989; "Methods and Compounds for AICA Riboside Delivery and for Lowering Blood Glucose," U.S. Ser. No. 466,979, filed Jan. 18, 1990; "Methods of Treating Neurodegenerative Conditions," U.S. Ser. No. 582,630, filed Sep. 12, 1990; and "AICA Riboside Analogs," U.S. Ser. No. 566,196, filed Aug. 10, 1991; the disclosures of which are incorporated herein by this reference.

Alternatively, extracellular concentrations of adenosine can be increased by the use of compounds which inhibit enzymatic degradation of adenosine. One group of such compounds includes inhibitors of adenosine deaminase, an enzyme which participates in the conversion of adenosine to inosine. Inhibitors of adenosine deaminase activity include coformycin, 2-deoxycoformycin, and erythro-9-(2-hydroxy-3-nonyl) adenine hydrochloride. Another group of such compounds includes inhibitors of adenosine kinase, which include 5'-amino, 5'-deoxy adenosine and iodotubercidin. These compounds are described in the commonly assigned patent application "Adenosine Kinase Inhibitors," U.S. Ser. No. 647,117, filed Jan. 23, 1991, the disclosure of which is incorporated herein by this reference.

Alternatively, extracellular concentrations of adenosine can be increased by the use of compounds which activate enzymes involved in the production of adenosine. One group of such compounds includes agents which enhance extracellular adenosine by stimulating AMP nucleotidase.

(3) Agents which inhibit the transport of adenosine include those which specifically inhibit cellular transport, and are essentially competitive inhibitors with adenosine, and other agents which inhibit adenosine transport nonspecifically. P-nitrobenzylthioinosine and dipyridamole appear to be competitive inhibitors, while a variety of other compounds, including colchicine, phenethylalcohol and papaverine inhibit adenosine transport nonspecifically.

(4) Interaction at the $A_1$ receptor can be increased by enhancers which increase the binding or intrinsic activity of either adenosine or adenosine agonists at the $A_1$ receptor (Bruns F., & Fergus J., Molecular Pharmacology 1990, 38:939-949). The class of compounds reported to show enhancement of $A_1$ activity include α-amino-3-benzoylthiophenes.

EXAMPLES

To assist in understanding the present invention, the following examples are described which include the results of several experiments. The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

EXAMPLE 1
HYPOTHERMIC AND PROTECTIVE EFFECTS OF CHA

Male gerbils weighing approximately 70-90 g were anesthetized with an halothane (3-4%):nitrous oxide:oxygen mixture (40:60). Both rectal and brain temperatures were monitored continuously and maintained within a range of 37°-38° C. throughout surgery. In a separate set of animals, rectal and brain temperature were maintained near normothermia for up to 4 hours after drug administration. Both common carotid arteries were exposed and at a designated time, Heifetz clamps were applied. At the end of 5 minutes both clamps were quickly removed, resumption of blood flow visually reassured and animals sutured closed. CHA was administered intraperitoneal (IP) at 5 minutes following reperfusion in approximately 0.2 ml of a phosphate buffered saline solution. Animals were housed 4 to a cage and allowed a 5-7 day recovery before sacrificing. Fixation of the brain was achieved by anesthetizing the animal, transcardially perfusing the brain with saline and then paraformaldehyde solution. Brains were removed and processed for paraffin embedding. Ten-micron paraffin sections were prepared and stained with cresyl violet and cells within the CA1 region of the dorsal hippocampus were counted by a person naive to the treatment.

TABLE 1

| EFFECT OF VARIOUS TREATMENTS FOLLOWING ISCHEMIA ON GERBIL HIPPOCAMPAL CA1 REGION CELL COUNTS | |
|---|---|
| TREATMENT | CELL COUNT (±SEM) |
| Control | 625 ± 22 |
| Ischemia (5 min) | 66 ± 14 |
| CHA (2 mg/kg) 5 min post Ischemia | 309 ± 42 |
| CHA (2 mg/kg) 5 min post Ischemia + Normothermia | 50 ± 4 |

A 5-minute period of ischemia resulted in a near total loss of CA1 cells, while CHA administration 5 minutes after the ischemic period provided a significant extent of protection. When the hypothermia effects of CHA were prevented by maintaining prolonged normothermia with heat lamp and blanket, however, CHA no longer provided protection. These results indicate that the previously observed neuroprotection shown when an agonist was administered or endogenous adenosine levels increased was likely the result of induced hypothermia rather than attenuation of EAA release. A reduction in core and brain temperature has been reported to be a potent cerebroprotectant when initiated prior to the ischemia insult or within 30 minutes following reperfusion. A 2°-3° C. drop in brain temperature is sufficient to achieve efficacy (Busto, R., et al., *J. Cereb Blood Flow Metab* 1987 7:729-738.)

Applicants measured the effect of CHA on body temperature following IP administration at the time points and doses indicated in FIG. 2. CHA was administered in isotonic saline (approximately 0.5 ml/animal) to male gerbils weight 80-90 gr. Temperature was recorded using a rectal probe which was allowed to equilibrate for at least 30 seconds prior to recording temperature.

The effect of the $A_1$ agonist CHA on body temperature following intracerebroventricular (ICV) administration was examined at the time points and doses indicated in FIG. 3. For ICV administration male gerbils weighing 80-90 gr. were lightly anesthetized with 2-4% halothane, skull cap exposed and hole drilled for access to the brain. A cannula was lowered 4 mm into the brain to allow infusion directly into the ventricle of 2 ul of artificial cerebrospinal fluid (CSF) (150 mM Na+, 3 mM K+, 1.4 mM Ca++, 0.8 mM Mg++, 1.0 mM Phosphate, 155 mM Cl−) containing CHA at the indicated concentrations. Drug solution was infused slowly over 1-2 minutes while cannula was allowed to remain in position for an additional 3 minutes. Following removal of cannula the skin flaps were sutured closed and the animal was removed from the halothane anesthesia. Colonic temperature was recorded at the times indicated in FIG. 3 using a rectal probe which was allowed to equilibrate for at least 30 seconds prior to recording temperature. Thus, applicants have demonstrated that the administration of CHA either IP or ICV can result in a significant and prolonged period of hypothermia.

EXAMPLE 2

EFFECT OF CHA ON GLUTAMATE RELEASE GLOBAL ISCHEMIA MODEL

Figure 4A:
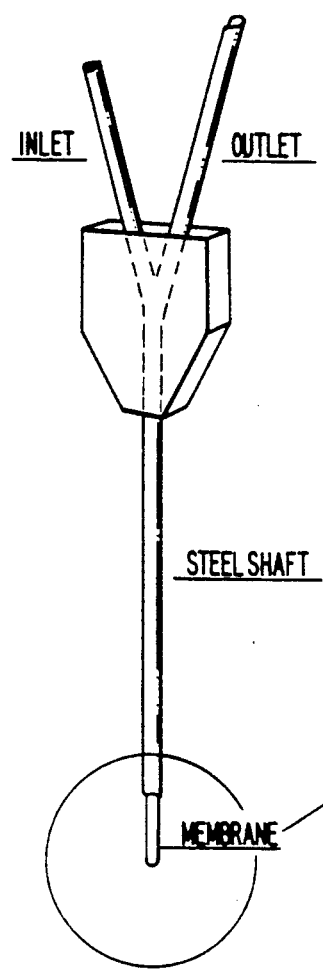
FIG. 4 illustrates the microdialysis probes used in the experiments described in EXAMPLES 2, 3 and 4. The probes allow perfusate to exchange with brain extracellular fluid across a dialysis membrane located at the tip of the probes.
Figure 4B:
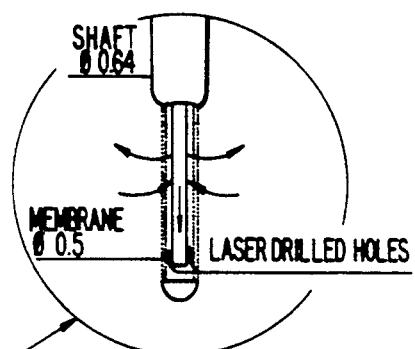

Rabbits were placed under surgical anesthesia, skull exposed and two small holes were drilled for placement of bilateral microdialysis probes at the level of the hippocampus. These probes, as shown in FIG. 4, allow perfusate to exchange with brain extracellular fluid across a dialysis membrane located on the tip of the probe. By including the drug in the perfusate solution, the probes also allow for delivery of a drug directly to the area where the probe is placed. Thus, one can measure the effect of a drug at a prescribed concentration on endogenous amino acid levels. The perfusate was serially collected and analyzed by high pressure liquid chromatography (HPLC) for the amino acid glutamate.

In these experiments, following placement of probes and drug infusion, rabbits were routinely exposed to a 10 minute period of brain global ischemia achieved by compression of the common carotid arteries. After the 10-minute ischemic period, reperfusion of blood to brain vasculature was instituted by releasing compression against the carotid arteries. Reperfusion was continued for an additional 80 minutes. The temporal sequence of events is outlined in FIG. 5 with the time scale made relevant to the initiation of ischemia which is designated as t=0. Perfusion of artificial cerebral spinal fluid (CSF) as in Example 1 (±drug) through the probe occurred at a rate of 2 μl per minute. Collection of perfusate for analysis was made on 20 minute samples prior to ischemia, 5 minute periods during ischemia and for two 5-minute periods into the reperfusion phase followed by a return to 20-minute collection periods. For each animal one side of the brain served as control while the contralateral side was drug-treated.

The results of an experiment using one concentration (1 μM) of CHA are displayed in FIG. 6. Amino acid concentrations at the various times were normalized for probe recovery by determining their percent change from baseline with baseline taken at t= −60. In control sides of the brains, there was a fairly constant level of glutamate prior to ischemia. During the ischemic insult there was an increase in glutamate levels 2-6 fold above control with a gradual return to basal levels shortly following reperfusion over a period of 30 minutes.

Figure 7A:
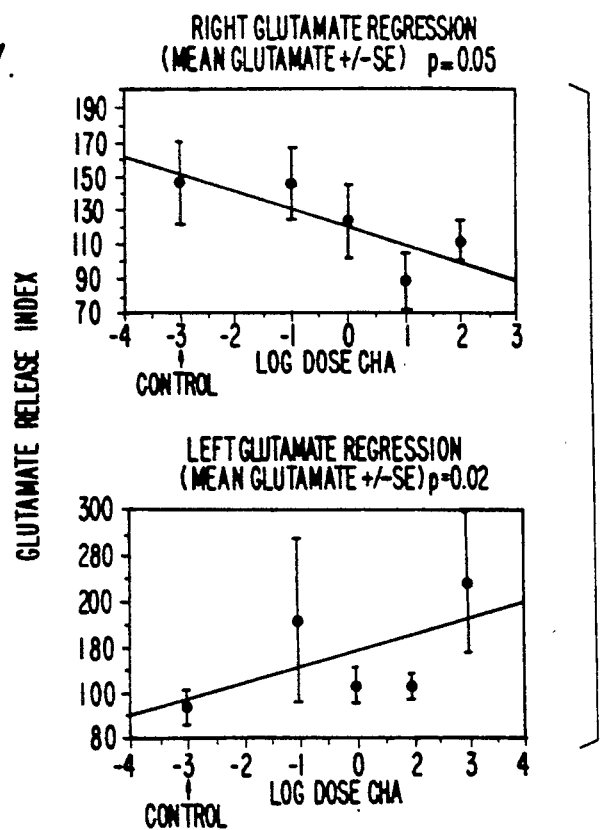
FIG. 7 depicts a regression analysis of the effect of various concentrations of CHA (0.1-100 μM) on (A) glutamate (GLU) release and (B) glycine (GLY) release during ischemia and reperfusion. The GLU or GLY release index equals the fractional increase in amino acid concentration versus time during ischemia and reperfusion according to the protocol in FIG. 5. CHA concentrations on the x-axis are expressed as log dose (μM). Data is shown for both the right side (CHA-treated) and the left side (control) of the brain.

The results obtained when CHA was present in the perfusate at varying concentrations are displayed in FIG. 7a. In these experiments, the effect of CHA on EAA release was examined over the range 0.1 μM to 100 μM CHA. The nature of the dialysis membrane on the probe allowed for the efficient exchange rate of approximately 20%. Accordingly, an infusion of CHA at 0.1 μM can be approximately translated into an effective brain concentration of 0.02 μM.

The data in FIG. 7a are expressed as the increase in amino acid concentration (GLU release index) from t=0 to t=80 versus the log CHA concentration (0.1/100 μM). Raising the concentration of CHA from 0.1 μM to 100 μM resulted in a significant ($p \leq 0.05$) dose dependent decrease in glutamate release during the ischemic period. By comparison, glutamate release from the control side of the brain appeared to be unaffected regardless of the concentration of CHA present in the perfusate on the contralateral side (p=0.2).

EXAMPLE 3

EFFECT OF CHA ON GLUTAMATE RELEASE FOCAL ISCHEMIA MODEL

Sprague-Dawley rats weighing approximately 250 g were housed 3-5 days prior to initiation of experiments. Surgery was performed under ketamine-induced anesthesia. Following induction of anesthesia each animal was placed on a Kopf stereotaxic device using ear bars and nose clamp for standardization of head position. The skull was exposed and with the aid of stereotaxic coordinates a 1 mm diameter hole was drilled to expose the dura and brain. Following nicking of the dura a microdialysis probe (BAS, Indianapolis, Ind.) was lowered to the level of the frontal-parietal cortex. This is the region of the brain most affected by loss of blood flow from the middle cerebral artery (MCA). A sample of a microdialysis probe is shown in FIG. 4. Each fraction number on the x-axis represents a 15 minute collection of perfusate. The probes were infused with either artificial CSF, as in Example 1, for controls or with CHA at the various indicated concentrations. The animals were then prepared for induction of a stroke episode by exposing the MCA and ipsilateral common carotid artery. Thirty minutes following the initial infusion of solution through the dialysis probe a stroke was induced by concomitant clamping of the MCA and ipsilateral common carotid artery. At 90 minutes following the initial clamping the clamps were removed, reflow through the MCA and common carotid visually reassured and exposed areas sutured closed. The animals were perfused through the microdialysis probes for an additional 60 minutes at which point the probes were removed and exposed brain areas sutured closed. All the animals were then allowed a reperfusion period of 22 hours at which point they were anesthetized with chloral hydrate for transcardial perfusion of the brain.

Figure 8B:
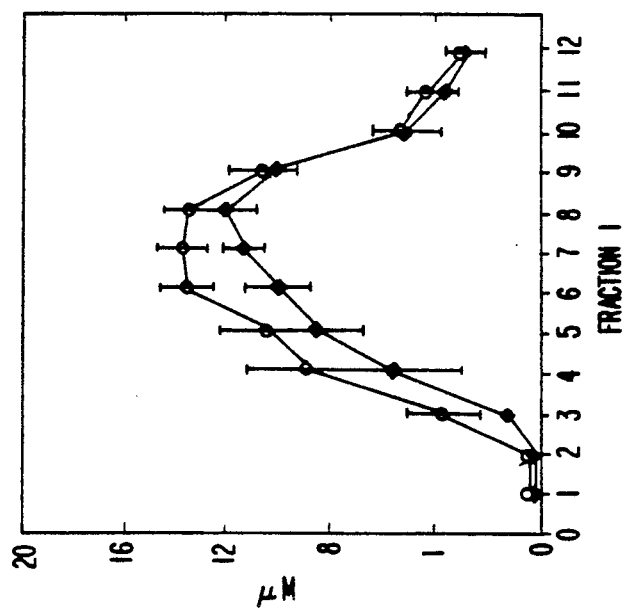
FIG. 8 depicts the effect of CHA at various concentrations ($10^{-5}$ to $10^{-9}$M) on glutamate release prior to, during focal stroke of 90 minutes, and during the reperfusion phase described in Example 4. Glutamate levels on the y-axis are expressed as μM in the perfusate from the dialysis probe. Collection periods are 15 minutes long, with periods 1 and 2 coming prior to focal stroke, periods 3–8 occurring during the 90 minute period of stroke, and periods 10–12 occurring during the reperfusion phase. Open circles (○) are values for control animals while filled circles (●) are values for CHA infused animals.
Figure 8A:
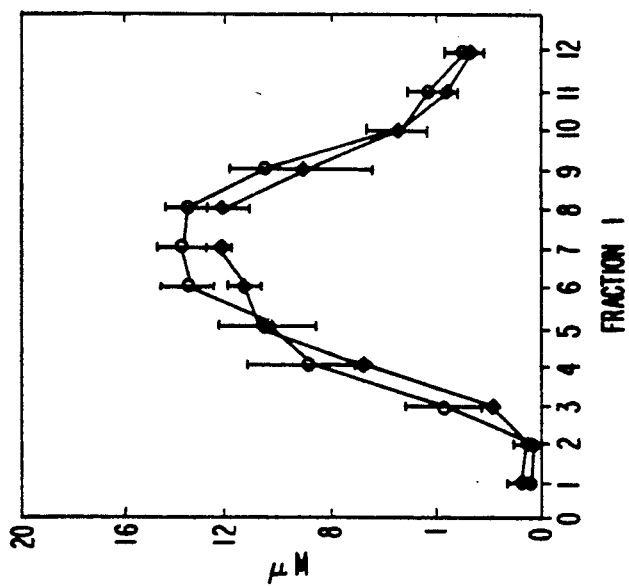
Figure 8E:
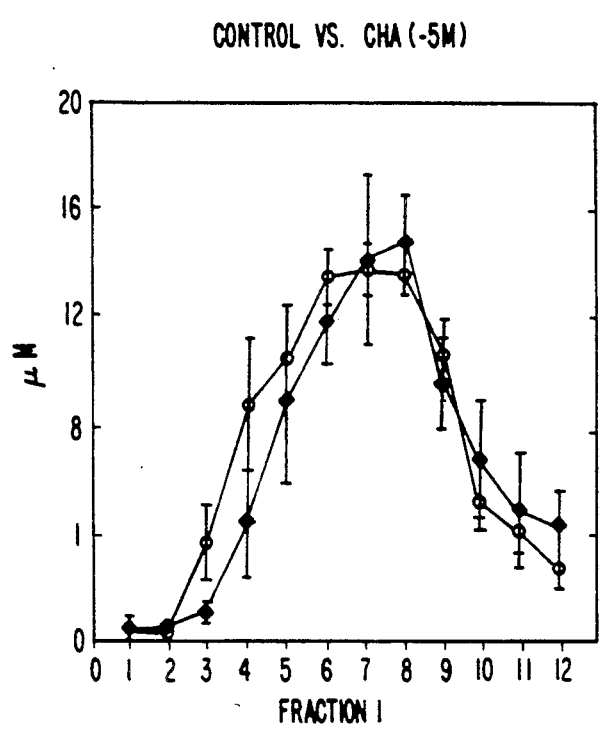

These experiments examined glutamate release prior to the stroke (fractions 1 and 2), during the stroke (fractions 3-8), and during the reperfusion phase of 60 minutes (fractions 9-12) (FIG. 8). In the control brains glutamate levels (○) increased 6-8 fold above baseline levels during the period (90 minutes) of middle cerebral artery obstruction. Subsequent to reperfusion glutamate levels returned to nearly basal values over the hour examined. When CHA was present in the perfusate at any concentration examined from 0.001 $\mu$M to 10 $\mu$M (●) there was no observable effect on basal glutamate levels, but there was a dose dependent attenuation of glutamate release during the period of stroke. While CHA at a concentration of 0.001 $\mu$M had no effect on glutamate levels compared to control samples, increasing its concentration 10 fold to 0.01 $\mu$M resulted in a significant attenuation of glutamate release. A similar extent of attenuation of EAA release was observed over a CHA concentration range from 0.01 to 1.0 $\mu$M. At higher concentrations of CHA (10 $\mu$M) there is no longer any effect of CHA on glutamate release during the period of obstructed blood flow.

Applicants have shown by the results in Example 3 that administration of a typical A1 agonist, CHA, will indeed attenuate excitatory amino acid release over a wide concentration range. In addition, applicants have shown that raising the concentration of the agonist can result in loss of the effect on EAA release. Because the agonist CHA has a selectivity ratio of approximately 400 fold (based on receptor binding analysis) for the A1 receptor compared to the A2 receptor, a possible explanation for the loss of effect on EAA release at higher concentrations of CHA is that the increased concentration of the agonist results in the activation of $A_2$ receptors, as well as $A_1$ receptors. Activation of A2 receptor has been reported to stimulate the formation of cAMP which itself is a stimulus for neurotransmitter release (Dolphin & Archer 1983, Neurosci Letts. 43:49–54).

EXAMPLE 4

EFFECT OF CHA ON GLYCINE RELEASE GLOBAL ISCHEMIA MODEL

Figure 9:
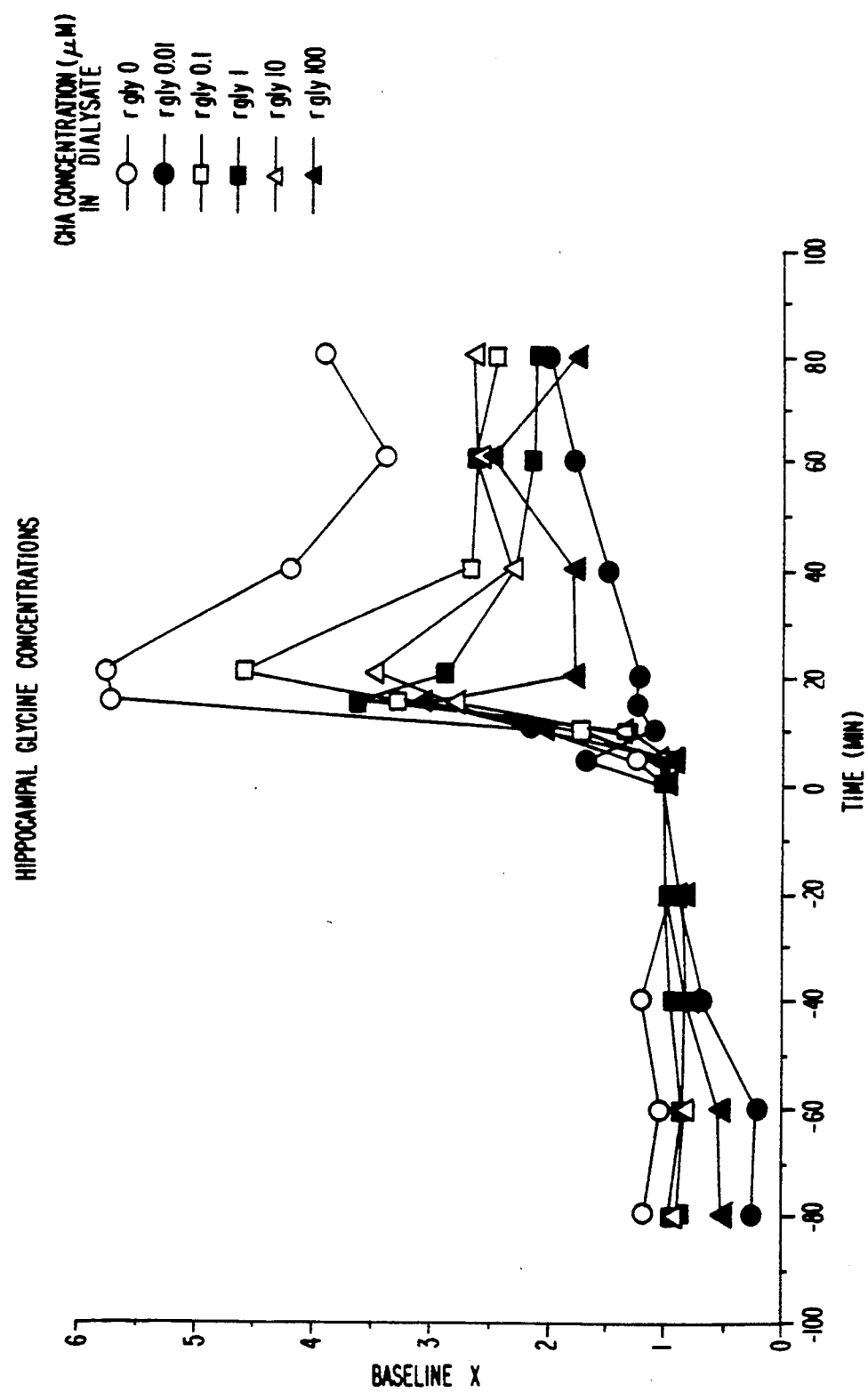
FIG. 9 depicts the effect of various concentrations of CHA on hippocampal glycine before, during and after ischemia consistent with the temporal sequence of events described in FIG. 5. Amino acid levels recorded on the y-axis are normalized to the level of glycine obtained at t=0.

The experimental paradigm used in the glycine studies was the same as that described in Example 2 for analysis of glutamate release during ischemia in rabbits. In fact, glycine was examined in the same perfusate samples in which glutamate was determined with one additional dose of 0.01 $\mu$M CHA (FIG. 9). In control animals with implanted dialysis probes, determination of glycine levels in the perfusate without added CHA showed a significant rise in extracellular glycine. This rise first became apparent at the end of the ischemia period (20 minutes). Glycine levels remained elevated well into the reperfusion period (20 minutes), decreased somewhat at 40 minutes and remained at this level for the entire time course of the experiment (80 minutes). Moreover, glycine levels at the 40-80 minute time period, while lower than observed at the 10 and 20 minute time points were, nevertheless, still significantly elevated compared to preischemia basal levels. When the adenosine agonist, CHA, was present in the perfusate, glycine levels were significantly attenuated at nearly all the time points examined. In addition, at the 10 and 20 minute time points there appeared to be a dose response relationship between CHA concentration and glycine levels. Beyond 20 minutes, however, CHA at all concentrations examined appeared to attenuate glycine levels to a similar extent.

Figure 7B:
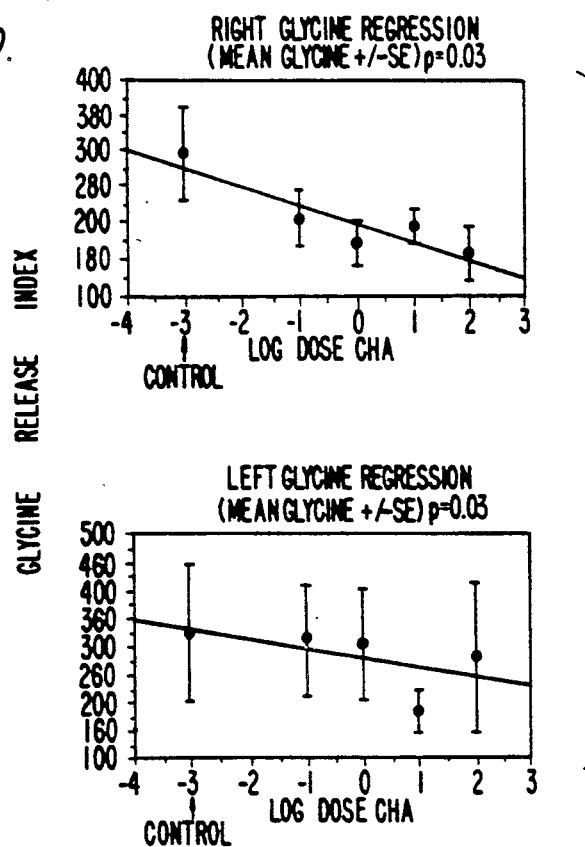

The addition of CHA to the perfusate at all the doses examined (0.01 $\mu$M-100 $\mu$M) caused a significant attenuation of glycine levels at nearly all time points following induction of ischemia (FIGS. 7b and 9). In addition, there appeared to be an inverse dose-response relationship between CHA concentration and glycine levels (FIG. 7b), that is, as CHA concentration was increased, glycine levels decreased.

Thus, applicants have demonstrated that CHA attenuates glycine release during ischemic insult to the brain. As noted in FIG. 1, a recognition (modulatory) site for glycine resides on the NMDA receptor complex. Activation of EAA receptors may involve any one of the four presently known EAA receptor subtypes (Miller, Pharmacology of Cerebral Ischemia, 1988, 139-149), one of which is the n-Methyl-D-aspartate (NMDA) receptor. Modulation of endogenous glycine levels can alter the responsiveness of the NMDA receptor complex to activation by presynaptically released glutamate. Therefore, the agonist-induced attenuation of extracellular glycine levels could decrease the level of activation of the NMDA receptor to glutamate, thus resulting in attenuation of cell death associated with persistent glutamate release.

EXAMPLE 5

EFFECT ON CHA ADMINISTRATION ON INFARCT VOLUME

Figure 10:
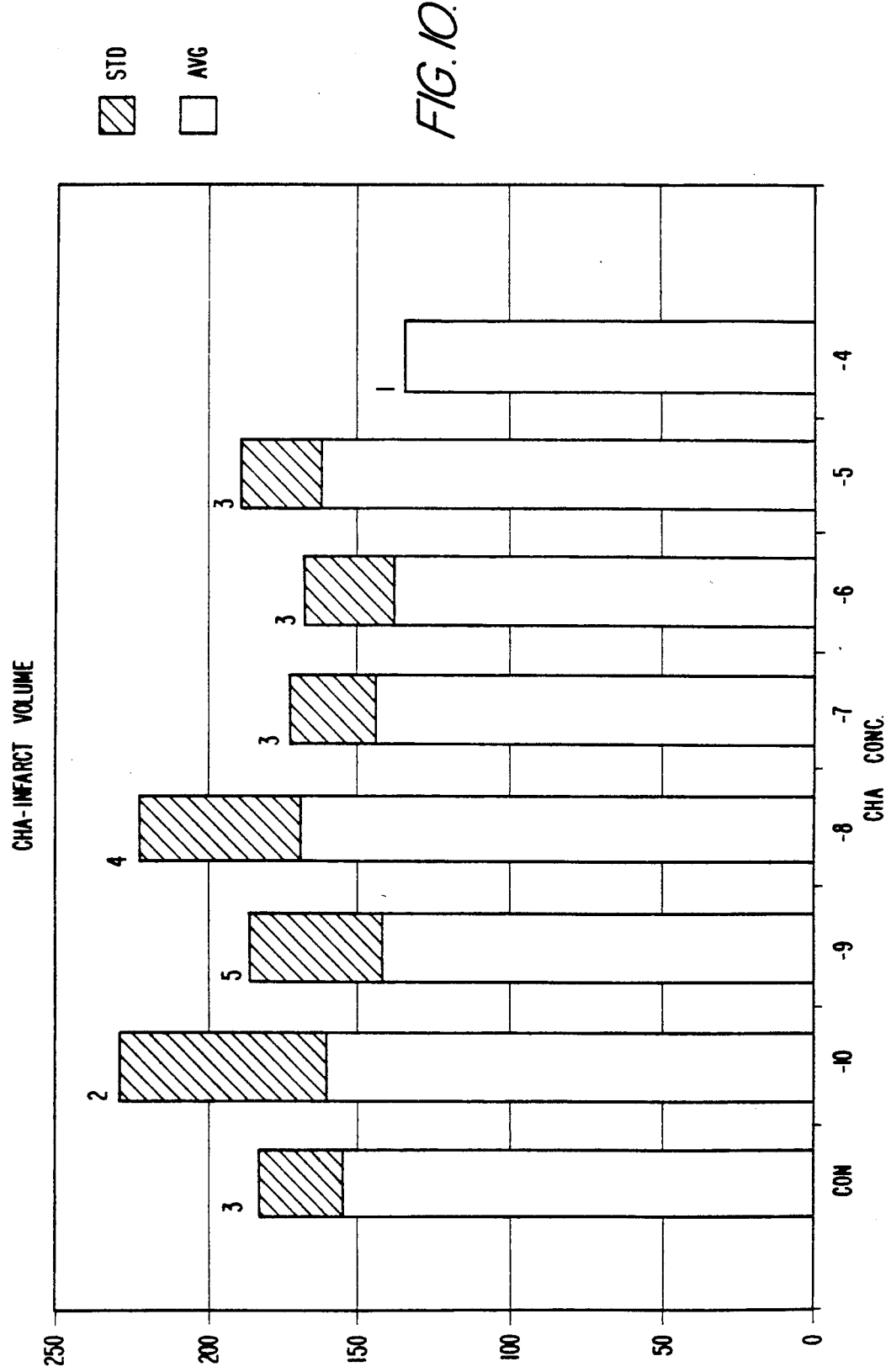
FIG. 10 depicts the stroke volume obtained from animals allowed to survive for 24 hours following a focal stroke of 90 minutes during which CHA was infused directly into the cerebral cortex at the various concentrations ($10^{-4}$ to $10^{-10}$M), but only during the procedure, as described in Example 4 and graphically presented in FIG. 9.

These experiments were performed on the same animals as in Example 3. All the animals were allowed a 24 hour survival after which animals were sacrificed. Brains were removed and, with the aid of a brain mold, sectioned into 2 mm slices with razor blades. Each slice was then exposed to triphenyltetrazolium HCL (TTZ) for staining of functional mitochondria. Viable brain tissue stained red while dead tissue which did not stain remained clear and was designated as the infarcted region. Infarct volume was quantitated using a Jandel Scientific digitizer and expressed as volume (mm$^3$). There was no effect of this brief (180 minutes) period of CHA administration at any of the concentrations examined on cortical infarct volume, as shown in FIG. 10, in spite of the reduction in extracellular EAA concentrations during the stroke period.

EXAMPLE 6

EFFECT OF LENGTH OF CHA INFUSION PERIOD ON INFARCT VOLUME

Spontaneously hypertensive rats weighing approximately 200 g were obtained from Charles River, Wilmington, Mass. and housed for 3-5 days prior to initiation of experiments. Surgery was performed under halothane (3-4%)-nitrous:oxide (40:60) anesthesia. Following induction of anesthesia each animal was placed on the Kopf stereotaxic device using ear bars and nose clamp for standardization of head position. The skull was exposed and with the aid of stereotaxic coordinates a 1 mm diameter hole was drilled to expose the dura and brain. An additional hole was drilled anterior to the initial hole for inserting a stainless steel screw. Following nicking of the dura, a stainless steel, 4 mm in length cannula obtained from Plastic Products, Roanoke, VA.

was implanted in the initial hole. The cannula was lowered 3 mm into the brain to access the central region of the cortex. Subsequently, a 1 µl solution of artificial CSF (see Example 1) containing no drug or CHA at either $10^{-9}$, $10^{-8}$, $10^{-7}$M concentration as indicated was infused over 10 minutes. The cannula was then connected directly to an Alzet pump (Palo Alto, Calif.) for continuous infusion of the same solution at a rate of 1 µl per hour for up to 24 hours. The animals were then prepared for induction of a stroke episode by exposing the MCA and ipsilateral common carotid artery. Thirty minutes following the initial infusion of CHA a stroke was induced by concomitant clamping of the exposed MCA and ipsilateral common carotid artery. The exposed areas with vessels still clamped were closed with minor suturing and the animals were allowed to come out of anesthesia. At 110 minutes following the initial clamping the animals were reanesthetized with halothane. The clamps were removed at exactly 120 minutes following the initial application of the clamps. Reflow through the MCA was visually assured and then exposed areas were sutured closed. All animals were allowed a reperfusion period of 22 hours at which point they were processed for determination of brain infarct volume exactly as described in Example 5.

Applicants have shown that to achieve neuroprotection in stroke the application of an adenosine agonist or adenosine regulating agent requires a continuous presence of the drug for more than 4 hours. Applicant's experiments are displayed in FIG. 11 and FIG. 12. The concentration of CHA was chosen based on the concentration needed to attenuate elevated glutamate levels in experiments described in Examples 2 and 3. Direct intracerebral infusion of CHA at $10^{-8}$M (FIG. 11) into the cortical area starting 30 minutes prior to stroke induction and continuing for 4 hours had no apparent effect on stroke volume measured 24 hours later. Moreover, as shown in Example 5, infusion of CHA over the concentration range $10^{-10}$M–$10^{-4}$M for 3 hours also had no effect on stroke volume recorded 24 hours later. However, when CHA at $10^{-8}$M (FIG. 11) or $10^{-7}$M (FIG. 12) was infused for 24 hours, the infarct volume measured at 24 hours was significantly decreased compared to control levels. Infusion of CHA at $10^{-9}$M for 24 hours had no significant effect on total infarct volume. Thus applicants have determined that it is necessary to obtain brain extracellular levels of the agonist or adenosine at concentrations sufficient to attenuate endogenous EAA release and to maintain these concentrations of the agonist in brain extracellular fluid for an extended period of time greater than 4 hours. Previous studies by Evans, et al., (Neurosci. Letts. 1987 83:287–293) examined multiple injections of the $A_1$ agonist 2 CLA (see page 5). However, they did not compare to a single injection and thus did not demonstrate a requirement for continuous or sustained treatment.

EXAMPLE 7

EFFECT OF CHA INFUSION PERISTROKE ON INFARCT VOLUME

Our experimental procedure is similar to that described in Example 6 except that the infusion of CHA was begun at 15 minutes after the MCA had been clamped. At this point, a cannula was lowered 3 mm into the brain to access the central region of the cortex. A 1 µl solution of artificial CSF containing CHA at $10^{-8}$M concentration was infused over 10 minutes. The cannula was then connected directly to an Alzet pump (palo Alto, Calif.) for continuous infusion of the same solution at a rate of 1 µl per hour for up to 24 hours. At 80 minutes following the initial clamping of the MCA, the animals were reanesthetized with halothane. The clamps were removed at 90 minutes following the initial application of the clamps and reperfusion through the MCA was visually assured prior to closing of the exposed areas with sutures. All animals were allowed a reperfusion period of 22 hours at which point they were processed for determination of brain infarct volume as described in Example 5. The results of these experiments are shown in FIG. 13 and Table 2.

Figure 13:
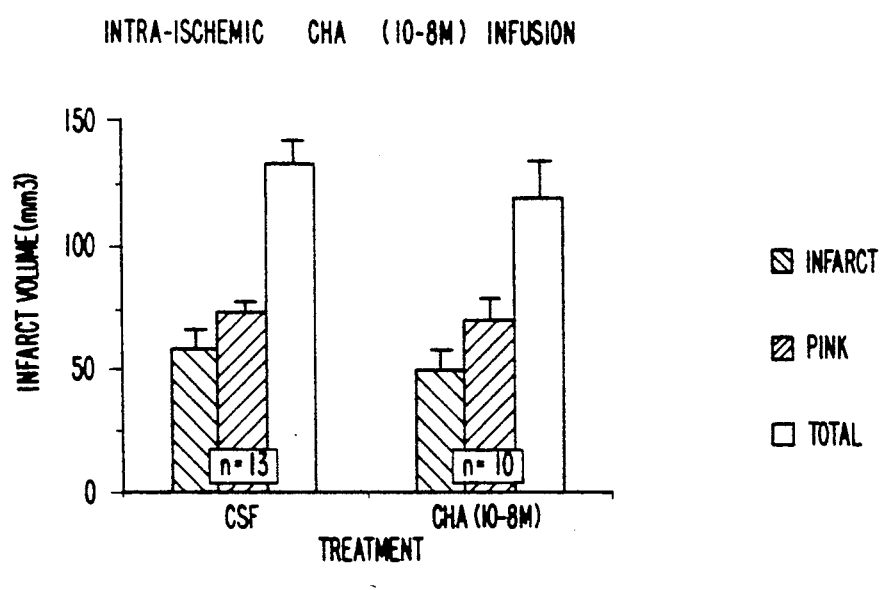
FIG. 13 depicts the effect of peristroke intracerebral administration of CHA ($10^{-8}$M) begun at 15 minutes following the initiation of a 90 minute focal stroke and continued until the time of sacrifice at 24 hours. Procedure is described in Example 6.

As shown in FIG. 13, CHA at $10^{-8}$M concentration was infused intracerebrally beginning 15 minutes following MCA clamp and continued for 24 hours until the animals were sacrificed. The results demonstrate no statistically significant effect of CHA when infusion is begun peri-ischemia in contrast to the results observed when CHA infusion is begun 30 minutes prior to initiation of the stroke. While there is no significant effect on stroke volume there is an observable effect when the data is analyzed on the individual slices (Table 2). In slice 5 at which level the cannula accesses the brain, there is a tendency for the infarct area to be less than the corresponding control levels suggesting that agonist administration may have benefits when administered peri-ischemia.

TABLE 2

EFFECT OF CHA ON TOTAL INFARCT VOLUME (in mm$^3$) IN SEQUENTIAL BRAIN SLICES

| BRAIN SLICE | CONTROL (n = 13) | CHA $10^{-8}$ (n = 9) |
|---|---|---|
| 1 | 2.8 ± 0.9 | 2.6 ± 1.7 |
| 2 | 19.6 ± 2.2 | 16.4 ± 3.5 |
| 3 | 28.0 ± 2.0 | 29.4 ± 2.9 |
| 4 | 33.2 ± 1.6 | 30.8 ± 3.2 |
| 5 | 28.5 ± 2.1 | 21.7 ± 3.4 |
| 6 | 15.1 ± 2.4 | 10.7 ± 2.9 |
| 7 | 5.2 ± 1.5 | 2.2 ± 0.8 |
| 8 | 0.4 ± 0.4 | 0.0 ± 0.0 |

Slice #1 is the most anterior section of the brain.

Thus, applicants have shown that agonist application in stroke could be applicable not only in a prophylactic setting but also in an emergency setting where patient is admitted with an ongoing stroke episode. However, there are clinical settings with a sizeable incidence rate of stroke where an $A_1$ agonist or adenosine regulating agent can be administered prophylactically to provide protection against brain damage. These clinical settings include carotid endarterectomy where an occluded atheromatous deposit in the carotid artery is excised, any neurosurgery which could compromise even briefly blood flow to the brain and coronary artery bypass graft surgery (CABG) which can result in neurological side effects in a number of patients.

Administration of Adenosinergic Agents

It is anticipated that adenosinergic compounds useful in the methods of the present invention will be effectively administered in amounts ranging from about 0.001 mg/kg/day to about 500 mg/kg/day, preferably from about 1 mg/kg/day to about 200 mg/kg/day. For the $A_1$ agonist adenosinergic compounds, a dosage of 0.01 to 10 mg/kg/day may be preferred because of the anticipated high potency at the $A_1$ receptor.

To deliver these adenosinergic compounds to patients, it is anticipated that they will most often be administered intravenously, since these compounds will be used in acutely ill patients. Potentially, the adenosinergic agents may be administered intrathecally to avoid the need to cross the blood-brain barrier. Compounds can also be administrated orally, by direct intramuscular injection, subcutaneously, topically to skin or mucous membranes, rectally, or by inhalation. Compositions acceptable for pharmaceutical use are well known. Prodrugs may also be utilized, i.e.. those which, when introduced into the body, metabolize to the active forms of the adenosinergic agents. The compounds may be administered using delayed release preparations, such as delayed release formulas and by devices such as minipumps.

In addition, adenosinergic compounds may be administered in the presence of a peripherally acting adenosinergic receptor antagonist. By peripherially acting adenosinergic receptor antagonist is meant an antagonist which does not penetrate the blood brain barrier. Such an approach would diminish peripheral side effects induced by the administration of an adenosinergic agent without affecting adenosinergic-mediated neural protection within the CNS.

We claim:

1. A method of preventing neural tissue damage caused by injury to the central nervous system of a warm-blooded animal comprising continuously administering to said warm-blooded animal a therapeutically effective amount of an adenosine agonist for a period of time sufficient to prevent neural tissue damage.

2. A method of preventing neural tissue damage caused by injury to the central nervous system of a warm-blooded animal comprising administering to said warm-blooded animal a plurality of doses of an adenosine agonist, said doses being spaced in time to maintain a therapeutically effective concentration in said central nervous system for a period of time sufficient to prevent neural tissue damage.

3. A method according to claim 1 or 2 wherein said time period for administration of said adenosine agonist is longer than 4 hours.

4. A method according to claim 1 or 2 wherein said period of time for administration of said adenosine agonist is longer than 8 hours.

5. A method according to claim 1 or 2 wherein said period of time for administration of said adenosine agonist is longer than 12 hours.

6. A method according to claim 1 or 2 wherein said period of time for administration of said adenosine agonist is longer than 24 hours.

7. A method according to claim 1 or 2 wherein said period of time for administration of said adenosine agonist is longer than 48 hours.

8. A method according to claim 1 or 2 wherein said therapeutically effective amount of adenosine agonist is the amount of said adenosine agonist which results in a concentration of said adenosinergic agent in the central nervous system of comparable potency to CHA at concentrations from $10^{-9}M$ to $10^{-6}M$.

9. A method according to claim 1 or 2 wherein said therapeutically effective amount of adenosinergic agent is the amount of said adenosine agonist which results in a concentration of said adenosine agonist in the central nervous system of comparable potency to CHA at concentrations from $10^{-8}M$ to $10^{-7}M$.

10. A method according to claim 1 or 2 wherein said adenosine agonist activates $A_1$ adenosine receptors for a period of time longer than 4 hours.

11. A method according to claim 10 wherein said adenosinergic agent has a ratio of affinity for $A_1$ receptors: $A_2$ receptors at least about 400:1.

12. A method according to claim 10 wherein said adenosinergic agent has a ratio of affinity for $A_1$ receptors: $A_2$ receptors of at least about 800:1.

13. A method according to claim 10 wherein said effective amount of said adenosine agonist is from 0.01 mg/kg/day to 10 mg/kg/day.

14. A method according to claim 1 or 2 wherein said effective amount of adenosine agonist is from 0.01 mg/kg/day to about 500 mg/kg/day.

15. A method according to claim 1 or 2 wherein said effective amount of adenosine agonist is from about 1 mg/kg/day to about 200 mg/kg/day.

16. A method according to claim 1 or 2 wherein said adenosine agonist crosses the blood brain barrier sufficiently to achieve levels in the cerebrospinal fluid and/or brain tissue which are at least 10% of plasma levels of said adenosine agonist.

17. A method according to claim 1 or 2 wherein said adenosine agonist is administered intrathecally.

18. A method according to claim 1 or 2 wherein said adenosine agonist is administered intravenously.

19. A method according to claim 1 or 2 wherein said adenosine agonist is administered orally.

20. A method according to claim 1 or 2 wherein said adenosine agonist is administered prophylactically.

21. A method according to claim 1 or 2 wherein said administration of said adenosine agonist is begun after said injury to the central nervous system.

22. A method according to claim 1 or 2 wherein said injury to the central nervous system is stroke.

23. A method according to claim 22 wherein said stroke is focal.

24. A method according to claim 1 or 2 wherein said injury to the central nervous system is brain trauma.

25. A method according to claim 1 or 2 wherein said injury to the central nervous system occurs during surgery.

26. A method according to claim 25 wherein said surgery is carotid endarterectomy.

27. A method according to claim 25 wherein said surgery is coronary artery bypass graft.

28. A method according to claim 25 wherein said administration of adenosine agonist is begun prior to surgery and continues during the surgery and for a period of longer than 4 hours after surgery.

29. A method according to claim 1 or 2 wherein said injury to the central nervous system is ischemia.

30. A method of attenuating-glycine release in a warm-blooded animal comprising administering an adenosine agonist to said warm-blooded animal.

31. A method of alternating glycine and excitatory amino acid release in a warm-blooded animal comprising administering to said warm-blooded animal an adenosine agonist.

* * * * *

UNITED STATES PATENT AND TRADEMARK OFFICE
CERTIFICATE OF CORRECTION

PATENT NO. : 5,236,908
DATED : August 17, 1993
INVENTOR(S) : Harry Gruber, et al It is certified that error appears in the above-indentified patent and that said Letters Patent is hereby corrected as shown below:

Column 8, line 25, please delete large space between were and monitored.

Signed and Sealed this

Twelfth Day of July, 1994

Attest:

BRUCE LEHMAN

Attesting Officer     Commissioner of Patents and Trademarks